United States Patent
Krogsgaard-Larsen et al.

[11] Patent Number: 4,960,769
[45] Date of Patent: Oct. 2, 1990

[54] 5,6,7,8-TETRAHYDRO-4H-ISOXAZOLO[4,5-C]-AZEPINE DERIVATIVES

[75] Inventors: Povl Krogsgaard-Larsen, Alleroed; Erik Falch, Vedbaek; Henrik Pedersen, Broenshoej, all of Denmark

[73] Assignee: H. Lundbeck A/S, Copenhagen-Valby, Denmark

[21] Appl. No.: 274,271

[22] Filed: Nov. 21, 1988

[30] Foreign Application Priority Data

Nov. 23, 1987 [GB] United Kingdom ............... 8727385

[51] Int. Cl.$^5$ .................... C07D 223/00; A61K 31/55
[52] U.S. Cl. ..................................... 514/215; 540/578
[58] Field of Search ......................... 540/578; 514/215

[56] References Cited

U.S. PATENT DOCUMENTS

4,608,378 8/1986 Falck et al. ..................... 514/302
4,859,666 8/1989 Eison et al. ..................... 540/578

OTHER PUBLICATIONS

Birdsdall N. J. M., Hulme E. C., and Burgen A. S. V. (1980), "The Character of Muscarinic Receptors in Different Regions of the Rat Brain", Proc. Roy. Soc. London (Series B) 207,1.
Watson M., Yamamura H. I., and Roeske W. R. (1983), "Aunique Regulatory Profile and Regional Distribution of [$^3$H]-Pirenzepine Binding in the Rat Provide Evidence for Distinct $M_1$ and $M_2$ Muscarinic Receptor Subtypes", Life Sci. 32, 3001–3011.
Krogsgaard-Larser et al., J. Neurochemistry, vol. 39, No. 5 (1982), pp. 1319–1324.

Primary Examiner—Nicholas S. Rizzo
Assistant Examiner—P. J. Dattow
Attorney, Agent, or Firm—Gordon W. Hueschen

[57] ABSTRACT

The present invention relates to novel compounds of the following formula:

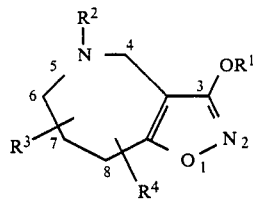

wherein $R^1$ is alkyl, alkenyl, alkynyl, branched or unbranched, with 1–6 carbon atoms either unsubstituted or optionally substituted with fluoro, hydroxy or phenyl, in which the phenyl group may be substituted with halogen, trifluoromethyl, lower alkyl, hydroxy or lower alkoxy;

$R^2$ is hydrogen or lower alkyl (1–6 C-atoms);

$R^3$ and $R^4$ are the same or different, and each represents hydrogen, alkyl (1–6 C-atoms) or cycloalkyl (3–6 C-atoms), or phenyl optionally substituted with halogen, trifluoromethyl, lower alkyl (1–6 C-atoms), hydroxy, or lower alkoxy (1–6 C-atoms) or phenyl-lower alkyl (7–10 C-atoms), in which the phenyl group may be substituted with halogen, trifluoromethyl, lower alkyl(1–6 C-atoms), hydroxy or lower alkoxy (1–6 C-atoms);

as well as individual isomers and pharmaceutically acceptable acid addition salts thereof.

The invention moreover, relates to methods for the preparation of the compounds of formula I, to novel intermediates, to pharmaceutical compositions containing same and to methods for the treatment of disorders, caused by malfunction of the acetylcholine (AcCh) or muscarinic system, by administering a non-toxic effective amount of a compound of formula I.

8 Claims, No Drawings

5,6,7,8-TETRAHYDRO-4H-ISOXAZOLO[4,5-C]-AZEPINE DERIVATIVES

BACKGROUND OF THE INVENTION

AcCh is known to be a neurotransmitter in the peripheral as well as the central nervous system (CNS). Reduced function of AcCh in the CNS, probably as a result of degeneration of neurones utilizing AcCh as a neurotransmitter, is believed to be related to the etiology of various diseases such as Alzheimer's disease and Down's syndrome (R. M. Marchbanks, *J. Neurochem.* 39 (1982) 9-15; R. D. Terry and P. Davies, *Ann. Rev. Neurosci.*, 3 (1980) 77; N. R. Sims, D. M. Bowen, S. J. Allen, C. C. T. Smith, D. Neary, D. J. Thomas and A. N. Davidson, *J. Neurochem.*, 40 (1983) 503-509; E. Roberts, in *Ann. New York Acad. Sci.* (F. Marott Sinex and C. R. Merril, editors), 396 (1982) 165-178. Furthermore, senile dementia, which may be associated with aging, appears to be somehow related to decreased AcCh activity in the CNS, and similarly impaired learning and memory functions have been associated with decreased functions of the central AcCh-system (P. S. Anderson and D. Haubrich, *Ann. Rep. Med. Chem.*, 16 (1981) 51-60.

Administrations of drugs which either increase the level of AcCh by blocking the enzymatic breakdown of the transmitter or directly stimulate the AcCh-receptor, AcCh-agonists, have been found to improve the cognitive malfunctions observed in patients with senile dementia of the Alzheimer type to various degrees (Christie et al., *Br. J. Psych.* 138 (1981) 138-146; Harbaugh et al., *Neurosurgery* 15 (1984) 514-518; Beller et al., *Psychopharmacol.* 87 (1985) 147-151; Schwartz and Kohlstaedt, *Life Sci.* 38 (1986); Summers et al., *N. Engl. J. Med.* 315 (1986) 1241-1245. Compounds capable of activating the AcCh receptors are therefore of primary interest. However, most known AcCh agonists, including AcCh itself, contain quaternary ammonium groups and, consequently, these compounds do not penetrate the blood-brain barrier (BBB) easily after peripheral administration. As a result of this, such compounds do not reach the AcCh receptors in the CNS but activate almost exclusively the peripheral AcCh receptors, which are unrelated to the diseases mentioned above, provoking various undesired effects.

Arecoline (methyl 1-methyl-1,2,5,6-tetrahydropyridine-3-carboxylate) is an AcCh agonist, which does not contain a quaternary ammonium group. Arecoline is a tertiary amine, and arecoline is capable of penetrating the BBB after peripheral administration. The ester group of arecoline is, however, very rapidly hydrolyzed in vivo, and arecoline has very weak and frequently negligible central effects after peripheral administration.

Previously, a series of 3-alkoxy-4,5,6,7-tetrahydroisoxazolo[4,5-c]pyridine derivatives (U.S. Pat. No. 4,608,378) with potent central cholinergic activity has ben described. These compounds may be considered as bioisosters of arecoline, in which the ester group has been replaced by a 3-alkoxy isoxazole unit, which is not susceptible to hydrolysis under physiological conditions.

DESCRIPTION OF THE INVENTION

According to the present invention it has now surprisingly been found that the novel compounds of formula I

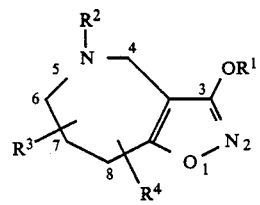

wherein
$R^1$ is alkyl, alkenyl, alkynyl, branched or unbranched, with 1-6 carbon atoms either unsubstituted or optionally substituted with fluoro, hydroxy or phenyl, in which the phenyl group may be substituted with halogen, trifluoromethyl, lower alkyl, hydroxy or lower alkoxy;
$R^2$ is hydrogen or lower alkyl (1-6 C-atoms);
$R^3$ and $R^4$ are the same or different, and each represents hydrogen, alkyl (1-6 C-atoms) or cycloalkyl (3-6 C-atoms), or phenyl optionally substituted with halogen, trifluoromethyl, lower alkyl (1-6 C-atoms), hydroxy, or lower alkoxy (1-6 C-atoms) or phenyl-lower alkyl (7-10 C-atoms), in which the phenyl group may be substituted with halogen, trifluoromethyl, lower alkyl (1-6 C-atoms), hydroxy or lower alkoxy (1-6 C-atoms);
as well as individual isomers and pharmaceutically-acceptable acid addition salts thereof, especially those compounds wherein $R^1$ is as defined in the foregoing, $R^2$ is hydrogen, $R^3$ is hydrogen, and $R^4$ is hydrogen or lower alkyl (1-6 C-atoms), and most especially the compounds 3-Ethoxy-5,6,7,8-tetrahydro-4H-isoxazolo[4,5-c]azepine,
3-Isopropoxy-5,6,7,8-tetrahydro-4H-isoxazolo[4,5-c]azepine,
3-(2-Propynyloxy)-5,6,7,8-tetrahydro-4H-isoxazolo[4,5-c]azepine,
3-(2-Butynyloxy)-5,6,7,8-tetrahydro-4H-isoxazolo[4,5-c]azepine,
(±+)-8-Methyl-3-(2-propynyloxy)-5,6,7,8-tetrahydro-4H-isoxazolo[4,5-c]azepine,
and pharmaceutically-acceptable acid addition salts thereof, have very potent AcCh agonist activity. The new 3-alkoxy-5,6,7,8-tetrahydro-4H-isoxazolo[4,5-c]azepine derivatives are considerably more potent than the derivatives previously described.

As examples of alkyl, alkenyl and alkynyl groups may be mentioned methyl, ethyl, n-propyl, iso-propyl, n-butyl, sec-butyl, n-pentyl, n-amyl, n-hexyl, allyl, 2-propenyl, 2-propynyl, 2-butynyl, or the like.

As examples of lower alkoxy may be mentioned methoxy, ethoxy, n-propoxy, isopropoxy, butoxy, amyloxy, or the like.

As examples of cyclo alkyl groups in formula I may be mentioned cyclopropyl, cyclopentyl, cyclohexyl, or the like.

The term "halogen" in Formula I designates preferably chlorine, fluorine or bromine.

The new compounds have high affinity to central cholinergic receptors, as measured by the ability of the compounds to displace tritiated oxotremorine-M from rat brain homogenates. The compounds have also high affinity to central muscarinic M-1 receptors, as defined by their ability to displace tritiated pirenzepine from rat brain homogenates.

The potent central activity of the compounds in vivo can be demonstrated by the ability of the compounds to induce hypothermia in mice or to prevent isoniazid induced convulsions in mice.

Compared with the potent central activity they show only minor peripheral side effects.

Moreover, the compounds of Formula I have very low toxicity as compared to therapeutic effective doses.

This invention also includes pharmaceutically acceptable salts of the compounds of Formula I formed with non-toxic organic or inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, oxalic, bis methylenesalicylic, methanesulfonic, ethanedisulfonic, acetic, propionic, tartaric, salicylic, citric, glucomic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is well-known to the art.

Specific examples of preferred compounds of formula I are:

3-Methoxy-5,6,7,8-tetrahydro-4H-isoxazolo[4,5-c]azepine (O-Methyl-THAO)
3-Ethoxy-5,6,7,8-tetrahydro-4H-isoxazolo[4,5-c]azepine (O-Ethyl-THAO)
3-Propoxy-5,6,7,8-tetrahydro-4H-isoxazolo[4,5-c]azepine (O-Propyl-THAO)
3-Isopropoxy-5,6,7,8-tetrahydro-4H-isoxazolo[4,5-c]azepine (O-Isopropyl-THAO)
3-Butoxy-5,6,7,8-tetrahydro-4H-isoxazolo[4,5-c]azepine (O-Butyl-THAO)
3-Allyloxy-5,6,7,8-tetrahydro-4H-isoxazolo[4,5-c]azepine (O-Allyl-THAO)
3-(2-Propynyloxy)-5,6,7,8-tetrahydro-4H-isoxazolo[4,5-c]azepine (O-Propargyl-THAO)
3-(2-Butynyloxy)-5,6,7,8-tetrahydro-4H-isoxazolo[4,5-c]azepine
(−+)-8-Methyl-3-(2-propynyloxy)-5,6,7,8-tetrahydro-4H-isoxazolo[4,5-c]azepine
(−+)-7-Methyl-3-(2-propynyloxy)-5,6,7,8-tetrahydro-4H-isoxazolo[4,5-c]azepine
(−+)-6-Methyl-3-(2-propynyloxy)-5,6,7,8-tetrahydro-4H-isoxazolo[4,5-c]azepine When $R^3$ and $R^4$ are different or the same on different positions, the compounds of Formula I can be separated into geometric and/or enantiomeric forms. Likewise, when $R^1$ contains a double bond the compounds of Formula I may exist in an E- and a Z-form. It is understood, that the present invention encompasses all enantiomers and mixtures thereof, as well as both the E- and the Z-forms and mixtures thereof.

The compounds of Formula I may-according to the invention-be prepared by
(a) reacting a compound of the Formula II

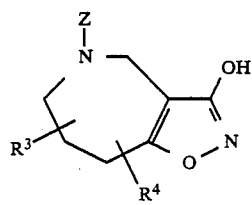

in which $R^3$ and $R^4$ are as defined above, and Z is an amino-protecting group readily removable, e.g. by hydrolysis or hydrogenation, with a compound of the Formula III $$R^1X \qquad \text{III}$$

in which $R^1$ is as defined above, and X is a leaving group, or $R^1X$ is diazomethane, and removing the group Z by hydrolysis or hydrogenation, or (b) reacting a compound of the Formula I, in which $R^2$ is hydrogen and $R^1$, $R^3$ and $R^4$ are as defined above, with an aldehyde of the Formula IV $$R^5-\overset{\overset{H}{|}}{C}=O \qquad \text{IV}$$

in which $R^5$ is hydrogen or lower alkyl, in the presence of a reducing agent, or (c) reacting a compound of the Formula I, in which $R^2$ is hydrogen and $R^1$, $R^3$ and $R^4$ are as defined above, with a compound of the Formula V $$R^2X \qquad \text{V}$$

in which $R^2$ and X are as defined above, or
(d) reacting a compound of the Formula VI

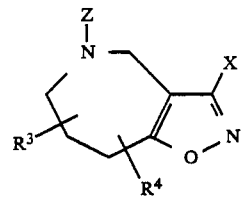

in which $R^3$, $R^4$, X and Z are as defined above, with an alcohol of the formula VII $$R^1-OH \qquad \text{VII}$$

in which $R^1$ is as defined above,
whereupon the compound of Formula I formed is isolated as the free base or preferably as a non-toxic pharmaceutically acceptable acid addition salt thereof, and optionally separated in individual isomers.

Specific examples of Z in formula II are the following:

Methoxycarbonyl, ethoxycarbonyl, propoxycarbonyl, tert.butoxycarbonyl, benzyloxycarbonyl, 4-chlorobenzyloxycarbonyl, trityl, formyl or acetyl.

As examples of leaving groups X may be mentioned chlorine, bromine, iodine.

In method (a) the reaction is preferably performed in a solvent, e.g. acetone, a lower alcohol, toluene or N,N-dimethylformamide in the presence of a base, e.g. potassium carbonate, a metal hydride, a tertiary amine, or a metal alcoholate. The reaction is carried out at a temperature from 0° C. to the boiling point of the solvent, and for a period of time from 1-96 hours. The removal of the group Z may be performed in wellknown manner, e.g. by hydrolysis or hydrogenation, and then, if desired, a group $R^2$ may be introduced by one of the methods (b) or (c).

In method (b) the reaction is performed in the presence of a reducing agent, e.g. formic acid, diborane or cyanoborohydride in a solvent, e.g. an ether, methanol, chloroform or dioxane, at a temperature from −10° C. to 100° C.

In method (c) the reaction is preferably performed in a solvent, e.g. acetone, a lower alcohol, toluene or N,N-dimethylformamide, in the presence of a base, e.g. potassium carbonate, a metal hydroxide, a tertiary amine or a metal alcoholate. The reaction is carried out at a temperature from 0° C. to the boiling point of the solvent and for a period of time from 0 to 96 hours.

In method (d) the reaction is normally performed in a solution of excess of the alcohol of formula VII, which may contain from 0% to 50% water, and in the presence of a base, e.g. a metal hydroxide or a metal alcoholate. The reaction temperature will usually be in the range of 0° C.-150° C., preferably from 0° C. to the boiling point of the alcohol of the formula VII. In many cases, especially when the reaction mixture contains water, the amino-protecting group Z is removed by hydrolysis during the reaction. Otherwise, the group Z may be removed in wellknown manner, e.g. by hydrolysis or hydrogenation, and then, if desired, a group $R^2$ may be introduced by one of the methods (b) or (c).

In the following, the invention shall be illustrated by examples which may not be construed as limiting.

EXAMPLE 1

Methyl 3-Methoxy-5,6,7,8-tetrahydro-4H-isoxazolo[4,5-c]azepin-5-carboxylate

To a solution of 490 mg (1.97 mmol) of methyl 3-hydroxy-5,6,7,8-tetrahydro-4H-isoxazolo[4,5-c]azepin-5-carboxylate (Formula II; Z=methoxycarbonyl, $R^3=R^4$=hydrogen) (P. Krogsgaard-Larsen, Acta Chem. Scand. B 31 (1977) 584–588) in ether (20 ml) was added an excess of diazomethane. The mixture was stirred at room temperature for 1 hour and the excess of diazomethane was destroyed by addition of glacial acetic acid. The mixture was evaporated in vacuo and the residue submitted to flash-chromatography on silica gel (eluent: toluene-ethyl acetate containing 1% of glacial acetic acid) yielding 270 mg of the title compound as a colourless oil. The oil was crystallized from toluene-light petroleum giving the analytically pure title compound. M.P. 68°-70° C. $^1$H NMR (CDCl$_3$): δ4.25 (2H, s), 3.93 (3H, s), 3.66 (5H, m), 2.83 (2H, t), 1.91 (2H, m).

EXAMPLE 2

Methyl 3-Ethoxy-5,6,7,8-tetrahydro-4H-isoxazolo[4,5-c]azepin-5-carboxylate

To a solution of methyl 3-hydroxy-5,6,7,6-tetrahydro-4H-isoxazolo[4,5-c]azepin-5-carboxylate (3,1 g, 14.6 mmol) in acetone (150 ml) was added potassium carbonate (5.02 g, 36.5 mmol). The suspension was stirred for 1 hour at 50° C., and ethyl bromide (3.3 ml, 43.8 mmol) was added. The mixture was refluxed for 16 hours and filtered. The filtrate was evaporated in vacuo. Water (75 ml) was added to the residue, and the mixture was stirred for 1 hour. The title compound (2.28 g, M.P. 51.5°-52° C.) was isolated by filtration. $^1$H NMR (CDCl$_3$): δ4.36 (2H, s), 4.07 (2H, q), 3.53 (3H, s), 3.43 (2H, t), 2.27 (2H, t), 1.80 (2H, m), 1.30 (3H, t).

EXAMPLE 3

Methyl 3-Isopropoxy-5,6,7,8-tetrahydro-4H-isoxazolo[4,5-c]azepin-5-carboxylate

The compound was synthesized by the method described in Example 2 by using isopropyl bromide instead of ethyl bromide, yielding 48% of the title compound as an oil.

$^1$H NMR (CDCl$_3$): δ4.23 (2H, s), 3.70 (5H, m), 2.80 (2H, t), 1.93 (2H, m), 1.36 (6H, d).

EXAMPLE 4

3-Ethoxy-5,6,7,8-tetrahydro-4H-isoxazolo[4,5-c]azepine Hydrochloride (Formula I; $R^1$=ethyl, $R^2=R^3=R^4$=hydrogen)

To a solution of sodium hydroxide (3.68 g, 92 mmol) in methanol (20 ml) and water (3 ml) was added 2.21 g (9.2 mmol) of methyl 3-ethoxy-5,6,7,8-tetrahydro-4H-isoxazolo[4,5-c]azepin-5-carboxylate (from Example 2) and the mixture was refluxed for 20 hours. The reaction mixture was evaporated in vacuo. The residue was dissolved in water and extracted three times with chloroform. The combined extracts were dried and evaporated. The residue was dissolved in ethanol and an excess of 4N Hydrochloric acid was added. The mixture was evaporated in vacuo yielding 1.7 g (84%) of the title compound. After recrystallization from acetonitrile the compound melted at 202°-203° C.

EXAMPLE 5

3-Methoxy-5,6,7,8-tetrahydro-4H-isoxazolo[4,5-c]azepine Hydrochloride (Formula I; $R^1$=methyl, $R^2=R^3=R^4$=hydrogen)

The compound was synthesized from methyl 3-methoxy-5,6,7,8-tetrahydro-4H-isoxazole[4,5-c]azepin-5-carboxylate (from Example 1) by the method described in Example 4. Recrystallization from methanol-ethyl acetate gave analytically pure title compound in a yield of 32%, MP 215°-217° C.

EXAMPLE 6

3-Isopropoxy-5,6,7,8-tetrahydro-4H-isoxazolo[4,5-c]azepine Hydrochloride (Formula I; $R^1$=isopropyl, $R^2=R^3=R^4$=hydrogen)

The compound was synthesized from methyl 3-isopropoxy-5,6,7,8-tetrahydro-4H-isoxazolo[4,5-c]azepin-5-carboxylate (from Example 3) by the method described in Example 4. Recrystallization from acetonitrile gave the analytically pure title compound in a yield of 37%, MP 218°-220° C.

EXAMPLE 7 tert.Butyl 3-Hydroxy-5,6,7,8-tetrahydro-4H-isoxazolo[4,5-c]azepin-5-carboxylate (Formula II; Z=tert.butyloxycarbonyl; $R^3=R^4$=hydrogen)

To a solution of 3-hydroxy-5,6,7,8-tetrahydro-4H-isoxazolo[4,5-c]-azepine hydrobromide (1.38 g, 5.9 mmol) (Formula I; $R^1=R^2=R^3=R^4$=hydrogen, X=oxygen) (P. Krogsgaard-Larsen, Acta Chem. Scand. B 31 (1977) 584–588) and potassium carbonate (1.62 g, 11.8 mmol) in water (20 ml) was added a solution of pyrocarbonic acid di-tert.butyl ester (1.54 g, 7.08 mmol) in tetrahydrofurane (10 ml) and the mixture was stirred at room temperature for 1 hour. The reaction mixture was evaporated in vacuo and the residue dissolved in water (20 ml). Ethyl acetate (100 ml) was added, and the mixture was cooled in an ice bath. The mixture was acidified with 2N hydrochloric acid to pH 6 and then to pH 3 with potassium hydrogensulfate. The phases were separated and the aqueous phase was extracted with two 50 ml-portions of ethyl acetate. The combined extracts were dried and evaporated in vacuo and the residue recrystallized from toluene-light petroleum yielding 887 mg (61%) of analytically pure title compound, MP 170°–171° C.

EXAMPLE 8 tert.Butyl 3-(2-Propynyloxy)-5,6,7,8-tetrahydro-4H-isoxazolo[4,5-c]azepin-5-carboxylate The compound was synthezised from tert.butyl 3-hydroxy-5,6,7,8-tetrahydro-4H-isoxazolo [4,5-c]azepin-5-carboxylate (from Example 7) and 2-propynyl bromide, by the method described in Example 4. The title compound was isolated by using chromatography on silica gel (eluent: toluene-ethyl acetate (3:1)) in a yield of 58%. $^1$H NMR: δ4.83 (2 H, d), 4.20 (2 H, s), 3.60 (2 H, t), 2.83 (2 H, t), 2.52 (1 H, t), 1.86 (2 H, m), 1.43 (9 H, s).

EXAMPLE 9

3-(2-Propynyloxy)-5,6,7,8-tetrahydro-4H-isoxazolo [4,5-c]azepine Hydrochloride (Formula I; $R^1$=2-propynyl, $R^2=R^3=R^4$=hydrogen)

To a solution of 530 mg (1.82 mmol) of tert.butyl 3-(2-propynyloxy)-5,6,7,8-tetrahydro-4H-isoxazolo[4,5-c]azepine-5-carboxylate (from Example 8) in ethyl acetate (10 ml) was added 10 ml of 1N solution of hydrochloric acid in ethyl acetate. The mixture was stirred at room temperature for 60 hours. The precipitate was collected and recrystallized from acetonitrile-ether yielding 267 mg (64%) of analytically pure title compound, MP 173°–175° C.

EXAMPLE 10

Ethyl 4-hydroxymethyl-3-oxopiperidine-1-carboxylate ethylene ketal

To an ice cooled solution of ethyl 4-carboxyethyl-3-oxopiperidine-1-carboxylate ethylene ketal (38 g, 0.132 mol, U.S. Pat. No. 4,278,676) in tetrahydrofurane (100 ml) is added lithium aluminium hydride pellets (2.51 g, 0.066 mol). The ice bath is removed and the reaction mixture is allowed to reach reflux temperature and is then kept at reflux temperature for 3 hours. The mixture is quenched with dilute hydrochloric acid and is diluted with dichloromethane. The mixture is washed twice with saturated brine, dried over magnesium sulphate and evaporated in vacuo to give 27.3 g (0.111 mol, 84%) of oily title product.

EXAMPLE 11

Ethyl 4-methyl-3-oxopiperidine-1-carboxylate ethylene ketal

A solution of ethyl 4-hydroxymethyl-3-oxopiperidine-1-carboxylate ethylene ketal (135 g, 0.55 mol) in dichloromethane (500 ml) and pyridine (100 ml) was treated with 4-toluenesulfonyl chloride (150 g) at 5° C. for 16 hours. Water (20 ml) is added, and the mixture is stirred for one hour at room temperature. The mixture was washed with dilute hydrochloric acid (3×200 ml) and dilute sodium hydroxide (2×200 ml). The organic phase was dried over magnesium sulphate and evaporated in vacuo to yield 178.2 g of an oil, which was dissolved in N,N-dimethylformamide (400 ml) and treated with sodium iodide (120 g) at 100° C. for 16 hours. The mixture was cooled, poured into water (1 liter) and extracted with ether (4×400 ml). The organic phase was washed with saturated calcium chloride (3×300 ml) and then dried over magnesium sulphate and evaporated in vacuo to yield an oil (147 g) which was dissolved in ethyl acetate (500 ml) and triethylamine (50 ml). 5% Palladium on charcoal (20 g) was added, and the mixture was shaken with hydrogen overnight (3.5 atm.) at room temperature. The catalyst was filtered off, and the solution was washed with water (100 ml) and saturated brine (3×100 ml). Drying over magnesium sulphate yielded oily title product (94 g, 0.41 mol, 75%).

The $^1$H-NMR spectrum showed a characteristic doublet at 0.85 ppm ($CH_3$-group).

EXAMPLE 12

Ethyl 4-methyl-3-oxopiperidine-1-carboxylate

To a solution of ethyl 4-methyl-3-oxopiperidine-1-carboxylate ethylene ketal (94 g, 0.41 mol) in tetrahydrofurane (200 ml) was added concentrated hydrochloric acid (200 ml), and the mixture was stirred for 16 hours at room temperature. Most of the tetrahydrofurane was evaporated in vacuo, and the residue was extracted with dichloromethane (3×200 ml). The organic phase was washed with saturated brine (2×150 ml), dried over magnesium sulphate and evaporated in vacuo to yield oily title product (60.1 g, 0.33 mol, 79%).

The $^1$H-NMR spectrum showed a characteristic doublet at 1.15 ppm ($CH_3$-group).

EXAMPLE 13 tert.Butyl 3-hydrox-8-methyl-5,6,7,8-tetrahydro-4H-isoxazole4,5-c azepin-5-carboxylate Ethyl 4-methyl-3-oxopiperidine-1-carboxylate (13.6 g, 0.074 mol) was transformed into the title compound by a series of steps analogous to those used in the preparation of tert.butyl 3-hydro-5,6,7,8-tetrahydro-4H-isoxazolo 4,5-c-azepin-5-carboxylate (Example 7, P. Krogsgaard-Larsen and Hjeds, Acta Chem. Scand. B 30 (1976) 884–88, and P. Krogsgaard-Larsen, Acta Chem. Scand. B 31 (1977) 58–88).

Yield: 2.5 g (0.0093 mol, 13%) of oily product.

The $^1$H-NMR spectrum showed a characteristic doublet at 1.05 ppm (8-methyl group) and a singlet at 1.50 ppm (tert.butyl group).

EXAMPLE 14

8-Methyl-3-(2-propynyloxy)-5,6,7,8-tetrahydro-4H-isoxazolo 4,5-c azepine, Fumarate tert.Butyl 3-hydroxy-8-methyl-5,6,7,8-tetrahydro-4H-isoxazolo 4,5-c azepin-5-carboxylate (0.5 g, 1.86 mmol) was transformed into the title compound hydrochloride in analogy with the procedure described in Examples 8 and 9. The oily hydrochloride was transformed into the fumarate in a conventional manner.

Yield: 80 mg (0.24 mmol, 13%) of analytically pure compound, M.P. 151°–152° C.

$^1$H-NMR (methanol-d$_4$): δ6.45 (2H, s); 4.85 (2 H, d); 4.06 (2H, s); 3.49 (3H, m); 3.33 (1H, t); 2.10 (2H, m); 1.41 (3H, d).

The following tests were used to assess the pharmacological effects of the compounds of Formula I.

$^3$H-oxotremorine M binding was performed essentially as described by Birdsdall et al., 1980. Briefly, rat brains were homogenized in 100 vol (w/v) 10 mM Na,K-phosphate buffer (pH 7.4) and aliquots incubated with $^3$H-oxotremorine M (84.9 Ci/mmol, NEN) alone or in the presence of test compound in a total volume of 1.5 ml for 40 min. at 30° C. The reaction was stopped by adding 5 ml ice-cold buffer and filtered through Whatman GF/B filters soaked previously in 0.1% polyethylenimin (Sigma) for minimum 30 min. The filters were washed once with the same volume of buffer, transferred to scintillation vials and extracted in scintillation fluid (Pico-fluor 15, Packard) for at least two hours before counted in a liquid scintillation spectrometer (Beckman LS 1800). Non-specific binding was estimated at 10 μM atropine and all estimations made in triplicate. At least two displacement curves were made for each compound tested.

$^3$H-pirenzepine binding was performed essentially as described by Watson et al., 1983, the conditions being very much the same as for $^3$H-oxotremorine binding, except that aliquots were incubated with 1.0 nM $^3$H-pirenzepine for 60 min. at 25° C. and that the reaction was stopped by direct filtration followed by 3 washes with 4 ml buffer.

Birdsdall N.J.M., Hulme E. C., and Burgen A,S.V. (1980). "The Character of Muscarinic Receptors in Different Regions of the Rat Brain". Proc.Roy.Soc. London (Series B) 207,1.

Watson M., Yamamura H. I., and Roeske W. R. (1983). "A unique regulatory profile and regional distribution of [$^3$H]-pirenzepine binding in the rat provide evidence for distinct M$_1$ and M$_2$ muscarinic receptor subtypes". Life Sci. 32, 3001–3011.

| Compound | Binding IC$_{50}$(nM) $^3$H—Oxo—M | $^3$H-Pirenzepine |
|---|---|---|
| Example 4 | 0.49 | 11 |
| Example 5 | 2.8 | 248 |
| Example 6 | 8.3 | 5 |
| Example 9 | 0.34 | 16 |
| Example 14 | 0.93 | 16 |
| O-Methyl-THPO | 62 | 8600 |
| Arecoline | 1.9 | 1000 |

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection. Results upon administration to human beings have been very gratifying.

Most conveniently the compounds of Formula I are administered orally in unit dosage form such as tablets or capsules, each dosage unit containing the free amine or a non-toxic acid addition salt of one of the said compounds in a amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

Typical examples of formulas for composition containing 3-ethoxy-5,6.7,8-tetrahydro-4H-isoxazolo[4,5-c]azepine hydrochloride (called O-Ethyl THAO, HCl for short) as the active ingredient, are as follows:

| (1) Tablets containing 5 milligrams of O-Ethyl THAO, HCl calculated as the free base: | |
|---|---|
| O-Ethyl THAO | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

| (2) Tablets containing 50 milligrams of O-Ethyl THAO, HCl calculated as the free base: | |
|---|---|
| O-Ethyl THAO | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |

| (3) Syrup containing per milliliter: | |
|---|---|
| O-Ethyl THAO | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

| (4) Solution for injection containing per milliliter: | |
|---|---|
| O-Ethyl THAO | 50 mg |
| Acetic acid | 17.9 mg |
| Sterile water | ad 1 ml |

| (5) Solution for injection containing per milliliter: | |
|---|---|
| O-Ethyl THAO | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, analgesics or antidepressants.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, involving the neurotransmitters acetylcholine and muscarine, by administering to a living animal body, including human beings, an adequate quantity of a compound of Formula I or a non-toxic acid addition salt thereof. An adequate quantity would be from about 0.001 mg to about 10 mg per kg of body weight per day, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

We claim:

1. A compound of the following formula:

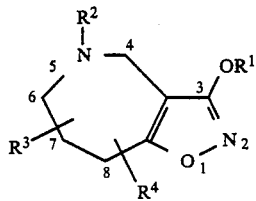

wherein $R^1$ is alkyl, alkenyl, alkynyl, branched or unbranched, with 1–6 carbon atoms either unsubstituted or optionally substituted with fluoro, hydroxy or phenyl, in which the phenyl group may be substituted with halogen, trifluoromethyl, lower alkyl, hydroxy or lower alkoxy;

$R^2$ is hydrogen or lower alkyl (1–6 C-atoms);

$R^3$ and $R^4$ are the same or different, and each represents hydrogen, alkyl (1–6 C-atoms) or cycloalkyl (3–6 C-atoms), or phenyl optionally substituted with halogen, trifluoromethyl, lower alkyl (1–6 C-atoms), hydroxy, or lower alkoxy (1–6 C-atoms) or phenyl-lower alkyl (7–10 C-atoms), in which the phenyl group may be substituted with halogen, trifluoromethyl, lower alkyl (1–6 C-atoms), hydroxy or lower alkoxy (1–6 C-atoms);

as well as individual isomers and pharmaceutically-acceptable acid addition salts thereof.

2. A compound according to claim 1, wherein $R^1$ is as defined in claim 1, $R^2$ is hydrogen, $R^3$ is hydrogen and $R^4$ is hydrogen or lower alkyl (1–6 C-atoms).

3. A compound according to claim 1 which is selected from:
3-Ethoxy-5,6,7,8-tetrahydro-4H-isoxazolo[4,5-c]azepine
3-Isopropoxy-5,6,7,8-tetrahydro-4H-isoxazolo[4,5-c]azepine
3-(2-Propynyloxy)-5,6,7,8-tetrahydro-4H-isoxazolo[4,5-c]azepine
3-(2-Butynyloxy)-5,6,7,8-tetrahydro-4H-isooxazolo[4,5-c]azepine
(−+)-8-Methyl-3-(2-propynyloxy)-5,6,7,8-tetrahydro-4H-isoxazolo[4,5-c]azepine,
and pharmaceutically acceptable acid addition salts thereof.

4. Compound of claim 1 being (−+)-8-Methyl-3-(2-propynyloxy)-5,6,7,8-tetrahydro-4H-isoxazolo[4,5-c]azepine as well as pharmaceutically acceptable acid addition salts thereof.

5. A pharmaceutical composition in unit dosage form comprising, as an active ingredient, a compound as defined in claim 1, and one or more pharmaceutical diluents or carriers.

6. A pharmaceutical composition in unit dosage form, according to claim 7, wherein the active ingredient is present in an amount from 0.1–100 milligrams per unit dosage.

7. Method for the treatment of disorders caused by malfunction of the acetylcholine (AcCh) or muscarinic system comprising the step of administering orally or parenterally to a subject in need of such treatment an effective amount of a compound of claim 1.

8. A method of claim 7, wherein the compound is administered in an amount from 0.1 to 100 mg per unit dosage.

* * * * *

UNITED STATES PATENT AND TRADEMARK OFFICE
CERTIFICATE OF CORRECTION

PATENT NO. : 4,960,769

DATED : Oct. 2, 1990

INVENTOR(S) : Povl Krogsgaard-Larsen, Erik Falch, Henrik Pedersen

It is certified that error appears in the above-identified patent and that said Letters Patent is hereby corrected as shown below:

Title Page, [56] References Cited, U. S. PATENT DOCUMENTS, first listing "Falck" should read -- Falch --.
Title Page, [56] OTHER PUBLICATIONS, 6th line down; "Aunique" should read -- A Unique --.
Title Page, [56] OTHER PUBLICATIONS, 10th line down "Krogsgaard-Larser" should read -- Krogsgaard-Larsen --.
Title Page, second line up from the bottom, Assistant Examiner - "P. J. Dattow" should read -- P. J. Datlow --.

Column 6, line 51; "-isoxazole" should read -- -isoxazolo --.
Column 9, line 65; "sheeps" should read -- sheep --.
Column 10, line 20; "-5,6.7,8-" should read -- -5,6,7,8- --.
Column 11, line 46/47 "abnormalies" should read -- abnormalities --.
Column 12, line 40; "-isooxazolo" should read -- -isoxazolo --.

Signed and Sealed this

Thirty-first Day of March, 1992

Attest:

HARRY F. MANBECK, JR.

*Attesting Officer*  *Commissioner of Patents and Trademarks*